United States Patent
Watanabe et al.

(10) Patent No.: US 10,154,788 B2
(45) Date of Patent: Dec. 18, 2018

(54) OBJECT INFORMATION ACQUIRING APPARATUS

(71) Applicant: CANON KABUSHIKI KAISHA, Tokyo (JP)

(72) Inventors: Tadaki Watanabe, Tokyo (JP); Koichiro Wanda, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 626 days.

(21) Appl. No.: 13/795,871

(22) Filed: Mar. 12, 2013

(65) Prior Publication Data
US 2013/0267856 A1 Oct. 10, 2013

(30) Foreign Application Priority Data
Apr. 5, 2012 (JP) .................................. 2012-086310

(51) Int. Cl.
*A61B 5/00* (2006.01)

(52) U.S. Cl.
CPC ............ *A61B 5/0095* (2013.01); *A61B 5/748* (2013.01); *A61B 5/0091* (2013.01); *A61B 5/743* (2013.01)

(58) Field of Classification Search
CPC ....... A61B 5/0091; A61B 5/095; A61B 5/743; A61B 5/748
USPC .......... 600/102; 606/130; 700/259; 398/133; 901/34
See application file for complete search history.

(56) References Cited

U.S. PATENT DOCUMENTS

| 2008/0167557 A1 | 7/2008 | Kozai ........................... 600/441 |
| 2010/0058870 A1 | 3/2010 | Kobayashi ...................... 73/596 |
| 2010/0286519 A1 | 11/2010 | Lee et al. ...................... 600/439 |
| 2010/0321324 A1 | 12/2010 | Fukai et al. ................... 345/173 |
| 2011/0161862 A1 | 6/2011 | Hibi et al. ..................... 215/781 |
| 2013/0114859 A1 | 5/2013 | Wanda .......................... 382/103 |
| 2013/0274585 A1 | 10/2013 | Wanda .......................... 600/407 |

FOREIGN PATENT DOCUMENTS

| CN | 201160859 | 12/2008 |
| CN | 102006828 | 4/2011 |
| CN | 102049330 | 8/2011 |

(Continued)

OTHER PUBLICATIONS

CN201160859Y, Shigenori, English Machine Translation, 55 pages.*

(Continued)

*Primary Examiner* — John P Leubecker
*Assistant Examiner* — Arnaldo Torres Diaz
(74) *Attorney, Agent, or Firm* — Venable LLP (57) ABSTRACT

Provided is an object information acquiring apparatus including: an irradiating unit that irradiates an object with light; a probe that receives an acoustic wave generated from the object irradiated with the light; a generating unit that generates an image of the object interior on the basis of the acoustic wave; an imaging region input unit that receives an input of a designation of an imaging region, which is a region of the object in which the acoustic wave is received by the probe; a display region input unit that receives an input of a designation of a display region, which is a region of the object in which the image generated by the generating unit is displayed; and a display unit that displays the generated image in the display region.

19 Claims, 8 Drawing Sheets

(56) References Cited

FOREIGN PATENT DOCUMENTS

| | | |
|---|---|---|
| EP | 2208467 | 7/2010 |
| JP | WO 2006/035381 | 4/2006 |
| JP | 2008-514264 | 5/2008 |
| JP | 2010-022812 | 2/2010 |
| WO | WO 2012/157221 | 11/2012 |
| WO | WO 2013/021574 | 2/2013 |

OTHER PUBLICATIONS

Extended European Search Report issued Jun. 25, 2013 in counterpart European Patent Application No. 13160540.4.
Office Action issued on Aug. 18, 2014, in counterpart Chinese (P.R.C.) patent application 201310106239.2, with translation.

* cited by examiner

OBJECT INFORMATION ACQUIRING APPARATUS

BACKGROUND OF THE INVENTION

Field of the Invention

The present invention relates to an object information acquiring apparatus.

Description of the Related Art

Photoacoustic imaging (PAI) is known as a photo-imaging technique using light. In photoacoustic imaging, a biological body, which is an object, is irradiated with pulse light. An acoustic wave generated in the examination segment such as tumor that has absorbed the pulse light energy is received by a probe. A received signal outputted from the probe is analyzed and optical property distribution in the biological body is acquired as image data.

Japanese Patent Application Laid-Open No. 2010-022812 (Patent Literature 1) discloses an apparatus in which a breast is held from both sides with a holding unit and an acoustic wave is received, while two-dimensionally scanning a probe above the holding unit. Such two-dimensional scanning of the probe makes it possible to acquire property information from a plurality of positions inside the object.

Japanese Translation of PCT Application No. 2008-514264 (Patent Literature 2) discloses an ultrasound apparatus in which a breast is held from both sides with a holding unit, and the direction of an ultrasound beam is controlled, while two-dimensionally scanning an ultrasound transducer array above the holding unit. By controlling the direction of the ultrasound beam, it is possible to acquire image data from either or both the part of a breast close to a chest wall that is not held by the holding unit and the part close to a nipple that is not in contact with a holding plate.

Patent Literature 1: Japanese Patent Application Laid-Open No. 2010-022812

Patent Literature 2: Japanese Translation of PCT Application No. 2008-514264

SUMMARY OF THE INVENTION

In the apparatus disclosed in Japanese Patent Application Laid-Open No. 2010-022812, the probe is two-dimensionally scanned in the main scanning direction and secondary scanning direction above the holding unit and the image of the scanned region is generated. However, there is a case in which an image is required to be generated in the region in which probe scanning is not performed.

When an image is generated with respect to the region in which the probe is not scanned, image reconstruction is performed using an acoustic wave incident obliquely on the probe from the object region and a voxel is produced. More specifically, an adequate delay is imparted and added to the acoustic wave received by a transducer array, and the received beam direction is bent, as in the ultrasound apparatus described in Japanese Translation of PCT Application No. 2008-514264. When image reconstruction is thus performed with respect to the region in which the probe is not scanned, the image quality is relatively degraded by comparison with that of the reconstructed image in the region where the probe has been scanned, due to problems associated with the directivity of the elements and reception sensitivity. In other words, the quality of the reconstructed image can be improved as the number of acoustic waves in the region where the probe is scanned is increased.

The portion of a breast close to a chest wall is an example of image reconstruction in the region where the probe is not scanned. In such a region, the probe cannot be scanned above the holding unit due to the presence of a plate-shaped unit supporting the chest wall. However, since a tumor can be also present in such a region, the user (health-care professional) can wish to obtain the image, even though of poor quality, for this region for some users.

In other words, the region that can be designated as an imaging region in photoacoustic imaging is restricted to the range in which the probe can be scanned, that is, to a zone above the holding unit surface, but the region for which the user wishes to display an image can be wider than the range in which the probe can be scanned. In such cases, when an acoustic wave is acquired from a range facing the transducer array by probe scanning, it is desirable that an acoustic wave from the periphery be acquired at the same time to perform image reconstruction. As a result, imaging of a large region necessary for the user can be performed.

In Japanese Translation of PCT Application No. 2008-514264, imaging of the region that actually cannot be scanned, such as the part of the breast close to the chest wall that is not held by the holding unit and the part close to the nipple that is not in contact with the holding plate, is performed by controlling the direction of the ultrasound beam. As a result, a region that is larger than usual can be acquired, but no means is provided for enabling the user to select whether to perform imaging of those regions in the imaging process.

The present invention has been created to resolve the above-described problem and it is an object thereof to provide an apparatus that performs photoacoustic imaging in which the user can select whether to display the image of the object region where the probe is not scanned.

The present invention provides an object information acquiring apparatus comprising:

an irradiating unit configured to irradiate an object with light;

a probe configured to receive an acoustic wave generated from the object irradiated with the light;

a generating unit configured to generate an image of an object interior on the basis of the acoustic wave;

an imaging region input unit configured to receive an input of a designation of an imaging region, which is a region of the object in which the acoustic wave is received by the probe;

a display region input unit configured to receive an input of a designation of a display region, which is a region of the object in which the image generated by the generating unit is displayed; and a display unit configured to display the generated image in the display region.

In accordance with the present invention, the user can select whether to display the image of the object region where the probe is not scanned in an apparatus that performs photoacoustic imaging.

Further features of the present invention will become apparent from the following description of exemplary embodiments with reference to the attached drawings.

DESCRIPTION OF THE EMBODIMENTS

In accordance with the present invention, the user can select whether to display an image also with respect to a region where the probe is not scanned, such as a chest wall side, when performing imaging by scanning the probe in the imaging region designated by the user. In this case, with respect to the region in which the probe is not scanned (that is, the image quality is poor) on the chest wall side, image reconstruction is performed after the selection has been received, or image reconstruction is performed without receiving the selection.

In the present invention, the term "acoustic wave" is inclusive of sound wave, ultrasound wave, photoacoustic wave, and light-induced ultrasound wave, and a receiver receives the acoustic wave that has propagated in the object. In other words, the object information acquiring apparatus of the present invention is inclusive of apparatuses using the photoacoustic effect according to which the acoustic wave generated inside an object by irradiating the object with light (electromagnetic wave) is received and property information on the interior of the object is acquired. In the case of the apparatuses using the photoacoustic effect, the acquired property information on the interior of the object indicates object information reflecting the initial sound pressure of the acoustic wave generated under light irradiation, a light energy absorption density derived from the initial sound pressure, absorption coefficient, or concentration of substance constituting the tissue. The concentration of substance is, for example, an oxygen saturation degree or oxy-deoxy hemoglobin concentration. Further, the property information may be also acquired as distribution information at each position in the object, rather than numerical data. In other words, distribution data such as absorption coefficient distribution or oxygen saturation degree distribution may be also acquired as image data.

The object information acquiring apparatus in accordance with the present invention may also be an apparatus using an ultrasound echo technique by which an ultrasound wave is transmitted toward an object, a reflected wave that has been reflected inside the object is received, and property information of the interior of the object is acquired. The property information acquired in the case of the device using the ultrasound echo technique reflects the difference in acoustic impedance between the tissues inside the object.

The preferred embodiments of the present invention will be described below with reference to the appended drawings. The dimensions, materials, shapes and mutual arrangements of constituent components described hereinbelow can be changed, as appropriate, according to various conditions or the configuration of the apparatus using the present invention, and the scope of the present invention should not be construed as being limited to the following description.

Embodiment 1

In the present embodiment, a method that enables the user to select whether to perform image reconstruction with respect to a region on the chest wall side is explained in relation to an apparatus in which photoacoustic imaging is performed by scanning a probe in a main scanning direction and a secondary scanning direction.

In the description below, first, the basic configuration and functions of each component of the apparatus are explained, and then a method for indicating an imaging region, which is a specific feature of the present invention, and a method for subsequent selection of a display region are explained. The term "imaging" in the description hereinbelow stands for a process of acquiring an acoustic wave generated when an object is irradiated with light. In some case, it may be inclusive of a process of creating an image of the interior of the object on the basis of the acoustic wave. In other words, the imaging in the present invention is a general concept corresponding to photoacoustic measurement or photoacoustic wave acquisition and can also include the conversion to an image.

Further, in the present invention, as will be described hereinbelow, an image of the object to be used for reference by the user is acquired with a camera, but this process is referred to as "acquisition of a reference image" and is distinguished from the abovementioned "imaging".

The region scanned by the probe and the region that is not scanned by the probe, which are referred to in the present description, are explained below. For example, considered is the case in which the object is held by plate-shaped holding units and a perpendicular line is dropped from a certain position A inside the object on the holding unit. When the probe can be moved to the position at the base of the perpendicular line, the position A is said to be within the region scanned by the probe. When a certain member, for example, a mechanism supporting the chest wall of the patient, is present at the position at the base of the perpendicular line and the probe cannot be moved thereto, the position A is said to be within the region that is not scanned by the probe. Summarizing, the region that is not scanned by the probe is a region that does not face the position of a transducer array during probe scanning. The image that can be generated in the region scanned by the probe is higher in quality than that generated in the region where the probe is not scanned.

Even when the position A is not strictly at the perpendicular line dropped from the probe, where the probe can be moved to a position at which the acoustic wave from the position A can be received with a sufficiently good element sensitivity, this position may be also considered to be a region that can be scanned by the probe.

(Basic Configuration of the Apparatus)

Figure 1:
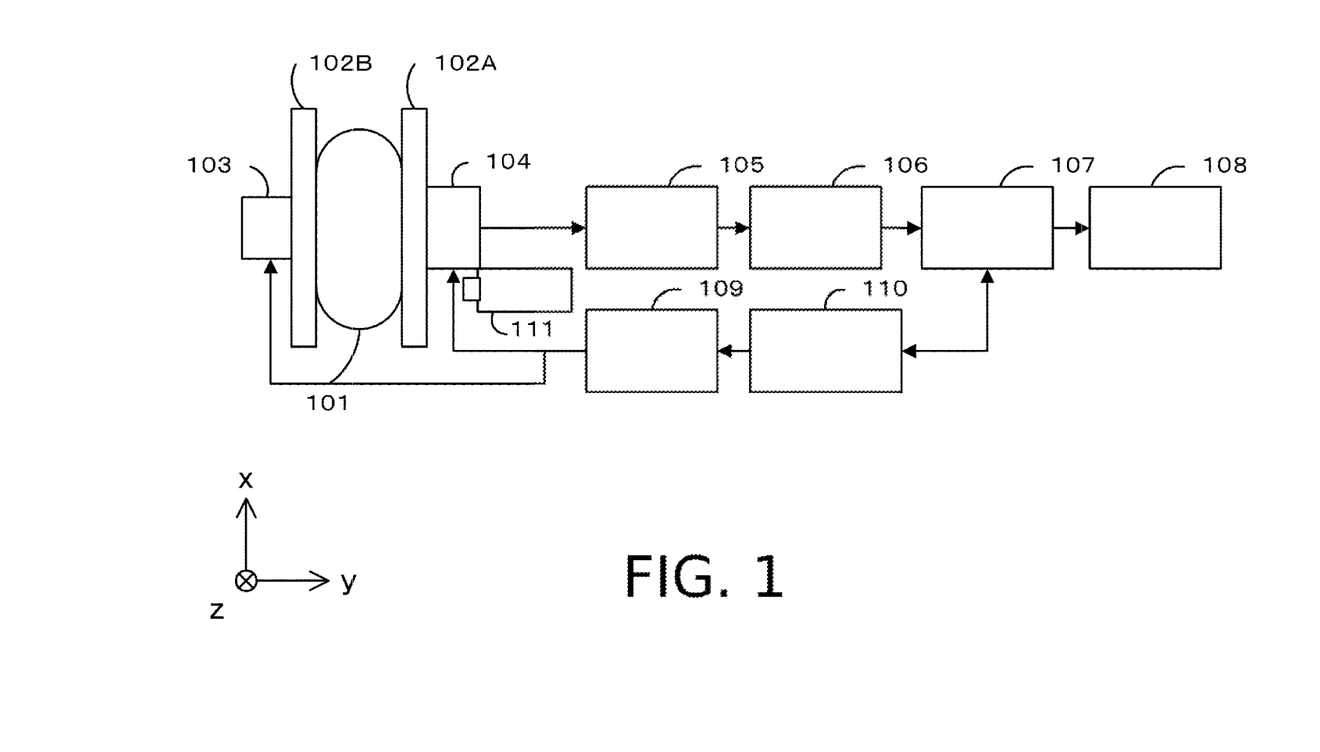
FIG. 1 is a block diagram of an object information acquiring apparatus in accordance with the present invention.

FIG. 1 is a schematic diagram illustrating the configuration of the object information acquiring apparatus in the present embodiment.

The object information acquiring apparatus of the present embodiment is provided with a holding unit 102 that holds a biological body 101 which is an object, an irradiating unit 103 that irradiates the objects with light, a probe 104 that receives an acoustic wave and converts the received wave into a received signal, and a measurement unit 105 that amplifies the received signal and converts it into a digital signal. The apparatus is also provided with a signal processing unit 106 that performs integration processing of the digitalized received signal, an image construction unit 107 that generates image data by using an output signal from the signal processing unit, and an image display unit 108 that displays the image generated in the image construction unit 107. The apparatus is also provided with a camera 111 that acquires a reference image to be used by the user for region designation, and a scanning control unit 109 for the irradiating unit 103 and the probe 104. The apparatus also includes a region input unit 110 that receives from the user an input relating to the region for which the reconstructed image is to be displayed and transmits the received input to the image construction unit 107.

Each of the constituent components will be described below in greater detail.

(Holding Unit)

For example, a breast can be considered as the biological body 101 serving as the object. The holding unit 102 is constituted by a pair of holding units, namely, a first holding unit 102A and a second holding unit 102B, that hold the biological body 101 such as a breast from both sides. The holding unit is typically a plate-shaped unit. The mutual arrangement of the two holding units is controlled by a holding mechanism (not shown in the figure) in order to change the holding gap and holding pressure. In the explanation below, when it is not necessary to distinguish the holding units 102A and 102B from each other, they will be together referred to as the holding units 102.

The biological body 101 is immobilized by placing the biological body 101 between the holding units 102, and a measurement error caused by the movement of the biological body 101 can be reduced. Further, the biological body 101 can be adjusted to the desired thickness according to the light penetration depth. Since the second holding unit 102B is placed on the optical path of the light, a material having a high transmittance with respect to the light used, such as polymethylpentene is preferred. Further, it is preferred that the first holding unit 102A on the probe 104 side have high acoustic compatibility with the probe 104.

The user opens a door (not shown in the figure) of a housing enclosing the constituent components, manipulates the biological body 101 and thinly stretches it or brings in close contact with the holding unit by using an acoustically compatible material. The holding unit 102 is then fixed, the door is closed, and imaging is started.

(Irradiating Unit)

The irradiating unit 103 that irradiates the biological body 101 with light is constituted by a light source generating light and an irradiating section that directs the light from the light source toward the object. A solid-state laser capable of generating pulsed light (a pulse width equal to or less than 100 nsec) having a central wavelength in a near-infrared region of 530 nm to 1300 nm is preferred as the light source. For example, an Yttrium-Aluminum-Garnet laser or a Titanium-Sapphire laser can be used. The light wavelength is selected between 530 nm and 1300 nm according to the light-absorbing substance (for example, hemoglobin, glucose, cholesterol, etc.) in the biological body which is the measurement target.

Examples of the irradiating section include a mirror reflecting the light, a lens changing the shape of the light beam by focusing or expansion of the light beam, a prism that disperses, refracts, and reflects the light, an optical fiber in which the light propagates, and a diffusion plate. Any irradiating unit may be used, provided that the desired region of the object can be irradiated with the light emitted by the light source and provided with the desired shape. The position of the emission tip (in other words, the irradiating region) of the light from the irradiating section is controlled by the scanning control unit 109.

(Probe)

The probe 104 is provided with a plurality of elements receiving the acoustic wave and converting the received wave into an electrical signal (received signal). Examples of the elements of the probe 104 include conversion elements using a piezoelectric phenomenon, conversion elements using optical resonance, and conversion elements using variations in electrostatic capacitance. Any elements may be used, provided that the acoustic wave can be received and converted into an electrical signal.

Since the sound pressure in the generated acoustic wave is proportional to light intensity, in order to increase the signal-to-noise ratio (SNR) of the received signal, it is desirable that the region on the front surface of the probe be irradiated. Therefore, it is desirable that the light emission tip of the irradiating unit 103 and the probe 104 be disposed at positions opposite each other, with the object being interposed therebetween. It is also preferred that scanning be synchronized by the scanning control unit 109 to maintain the mutual arrangement of the light emission tip and the probe 104. The biological body 101 can be also irradiated with light from the same side as the probe 104 by also guiding the light from the irradiating section to the probe 104 side.

(Measurement Unit)

The measurement unit 105 is constituted by a signal amplification unit that amplifies the analog signal (analog received signal) inputted from the probe 104 and an A/D conversion unit that converts the analog signal into a digital signal. In the signal amplification unit, the control is performed to change the amplification gain according to the period of time from light irradiation till when the acoustic wave reaches the probe elements in order to obtain image data having uniform contrast regardless of the depth in the biological body.

(Signal Processing Unit)

The signal processing unit 106 performs sensitivity spread correction of the elements correspondingly to the digital received signal outputted from the measurement unit 105, complementary processing of physically or electrically defective elements, recording to a recording medium (not shown in the figure), integration processing for noise reduction, and the like. In the integration processing, the reception of the acoustic wave is performed repeatedly in the same scanning position of the biological body 101 and the received signal is averaged to reduce the system noise and increase the SNR of the received signal.

(Image Construction Unit)

The image construction unit 107 generates as image data a distribution representing optical property information at each position in the biological body 101 by using the signal outputted from the signal processing unit 106. Such processing is also called image reconstruction processing, and the generated image is called a reconstructed image. Various types of correction processing performed to adjust the brightness, correct distortions, and cut out the region of interest may be used to obtain the image data better suitable for diagnostics. The image construction unit corresponds to the generating unit in accordance with the present invention. The reconstructed image corresponds to the generated image in accordance with the present invention.

In the image construction unit 107, as will be described hereinbelow, the image of the imaging region indicated by the user in the region input unit 110 is reconstructed and image data are sent to the image display unit. In addition, according to the user's selection, the image of the chest wall portion is reconstructed. However, since the image of the region on the chest wall side has poor quality, information relating to the boundary of the regions with different image quality may be added to the image data sent to the image display unit.

(Image Display Unit)

The image display unit 108 is a display device that displays the image property distribution by using the image data inputted from the image construction unit 107. The image display unit corresponds to the display unit in accordance with the present invention.

(Scanning Control Unit)

As mentioned hereinabove, the scanning control unit 109 controls the scanning positions of the light emission tip and the probe 104. A wide range can be measured even with a small probe by performing two-dimensional scanning thereof with respect to the biological body 101 and receiving the acoustic wave at each scanning position. The scanning range of the light emission tip and the probe 104 is determined according to the control results of the below-described region input unit 110.

(Region Input Unit)

The region input unit 110 is input means for designating an imaging region. The imaging region, as referred to herein, is a range in which a three-dimensional photoacoustic signal is acquired by the probe in the object 101 held by the holding unit 102. A combination of a pointing device such as a mouse and a keyboard with a display device, or a pen tablet may be used as the region input unit 110. A reference image when the region is designated may be displayed at the image display unit 108 or at a separate display device. As mentioned hereinabove, the scanning control unit 109 to which the imaging region inputted by the user has been transmitted controls the scanning position of the light emission tip and the probe 104 so that the acoustic wave from the imaging region could be acquired. The received signal based on the acquired acoustic wave is reconstructed in the image construction unit 107 to obtain image data. In terms of inputting the imaging region, the region input unit corresponds to the imaging region input unit in accordance with the present invention.

The region input unit 110 has means for receiving the user's selection as to whether to perform image reconstruction of the region on the chest wall side.

When the image of the region on the chest wall side is reconstructed, as will be described below in greater detail, it is necessary that the light emission tip and the probe 104 be scanned over a portion, in the end section of the scannable region, adjacent to the chest wall (this portion is the upper end when the patient is in the prone position and the breast hangs down), and the acoustic wave from the chest wall portion be acquired. Therefore, the user may be able to select the display of the reconstructed image on the chest wall side only when the imaging region designated by the user in the region input unit 110 is scanned in the end section of the scannable range close to the chest wall. The user can recognize that region reconstruction on the chest wall side is also possible by the display in the region input unit 110. In terms of designating whether to display the reconstructed image obtained on the chest wall side, the region input unit corresponds to the display region input unit in accordance with the present invention. Further, the object region on the chest wall side in this case corresponds to the adjacent region in accordance with the present invention.

(Camera)

The camera 111 acquires the reference image indicating the form of the biological body 101 that has been compressed and held. The user refers to the reference image when designating the imaging region. The reference image is transmitted to the region input unit 110. The camera 111 is disposed at a view angle such that the maximum range that can be designated by the user as the imaging region can be seen.

Figure 2:
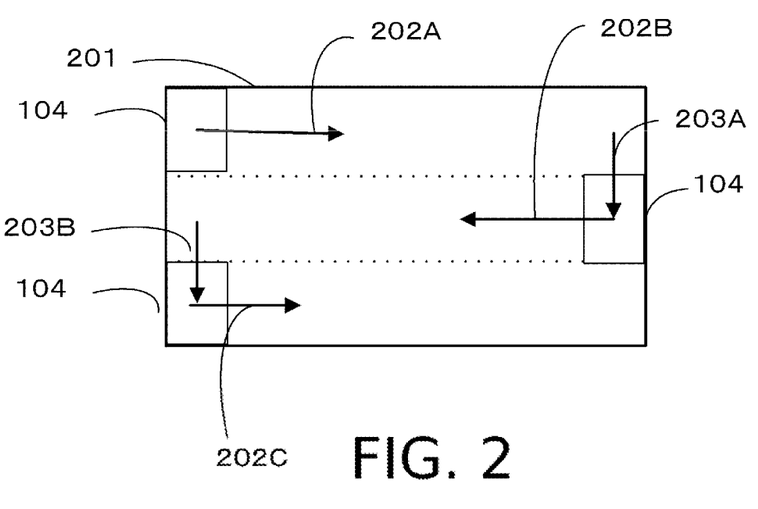
FIG. 2 is a conceptual diagram illustrating the movement of a probe.

As shown in FIG. 2, the probe 104 is scanned in the main scanning direction shown by the reference numeral 202 and also scanned in the secondary scanning direction represented by the reference numeral 203 in order to receive the photoacoustic wave of the imaging region 201. In the figure, the designated imaging region 201 from the breast hanging down from the patient in a prone position is observed from the side of the first holding unit 102A. Therefore, in the figure, the upper side corresponds to the portion close to the chest wall of the patient. As a result, in order to pick up the image on the chest wall side, it is necessary to scan the segment in which the imaging region 201 is adjacent to the chest wall portion, that is, the uppermost end (patient side) of the scannable region of the probe.

(Flow of Imaging Region Indication Method)

Figure 3:
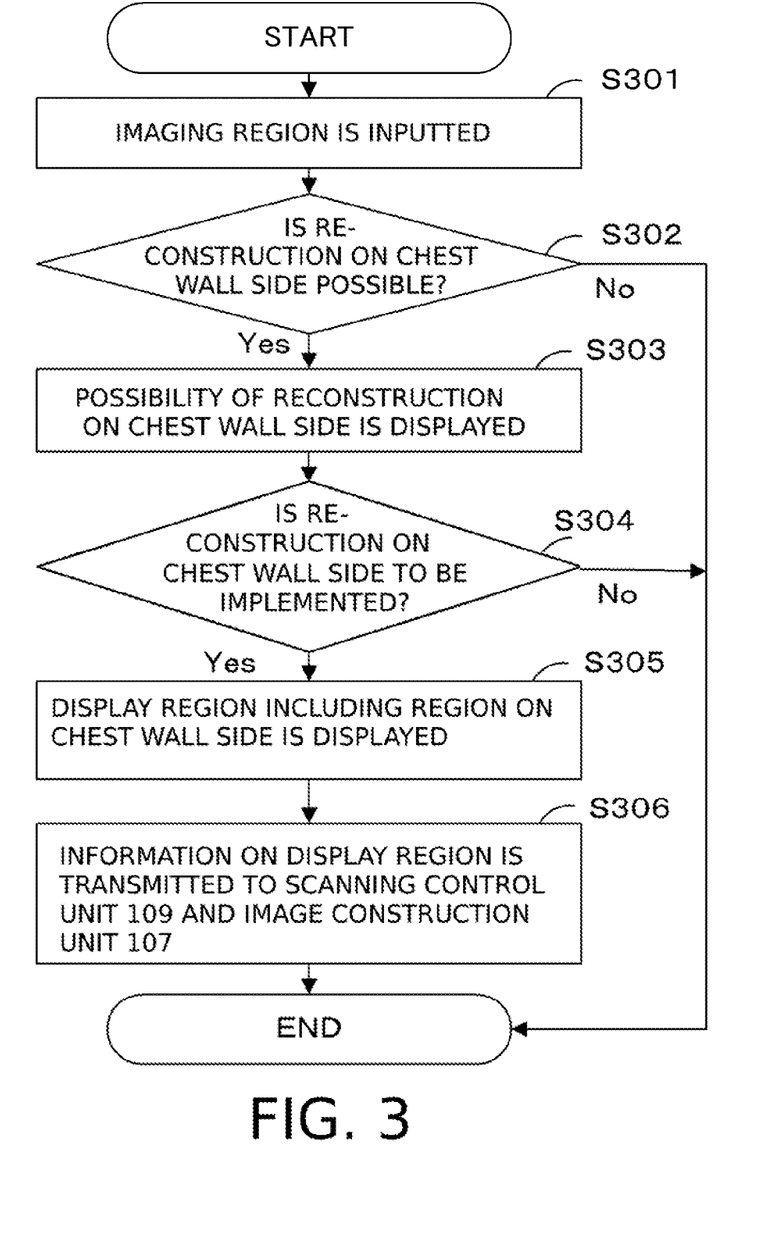
FIG. 3 is a flowchart illustrating the imaging sequence on the chest wall side in Example 1.

The flow of processing of selecting whether to reconstruct the image of the region on the chest wall side (region with poor image quality) in addition to the region with good image quality in the region input unit 110 of the present embodiment will be explained below with reference to FIG. 3. FIG. 3 is a flowchart illustrating the processing implemented when the imaging region of the present embodiment is designated.

The processing in FIG. 3 is started when the user sets a region for performing image reconstruction in the region input unit 110.

Figure 4:
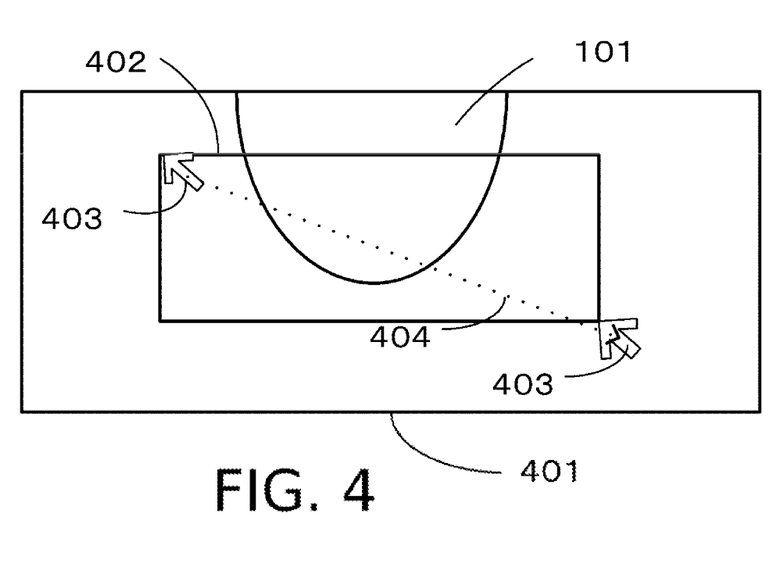
FIG. 4 is a conceptual diagram illustrating an input method for an imaging region.

In step S301, the user designates the imaging region. The conceptual diagram shown in FIG. 4 illustrates how an imaging region 402 is designated by using a reference image 401 representing the biological body 101. The user designates the position and region for photoacoustic measurements by using the region input unit. The user thus can designate the imaging region 402 on the reference image and, therefore, can designate exactly the imaging position and region.

Where the imaging region 402 is designated by the user, the region input unit 110 automatically determines the imaging region 402 such as shown in FIG. 4 from the scanning range of the probe 104 on the holding unit 102 and the distance between the holding units 102. In region designation, any region may be designated by a pointing device and the region displayed as the initial state may be changed. In FIG. 4, a rectangular region 402 is designated by moving a cursor 403 from the upper left corner to the lower right corner along a trajectory 404 by dragging a mouse.

In step S302, the region input unit 110 determines whether to scan the upper end of the scannable range with the emission tip and the probe 104 when imaging the imaging region inputted in step S301. When the upper end of the scannable range is scanned, it is determined that the image on the adjacent chest wall side can be also reconstructed. Where the reconstruction is determined to be possible (S302=YES), the processing advances to step S303. Meanwhile, where it is determined that the reconstruction is impossible (S302=NO), the present flow is ended and the imaging is performed as usual with respect to the designated imaging region.

In step S303, the possibility of reconstructing the image on the chest wall side is displayed for the user. This display is performed, for example, in a format selectable by the user, as shown in a check box 501 in the lower right corner of FIG. 5. The configuration in which the check box 501 is displayed at all times at the region input unit 109 and the check box 501 is checked only when the reconstruction on the chest wall side is possible, or the configuration in which the check box 501 is displayed only when the reconstruction of the chest wall side is possible may be used.

Figure 5:
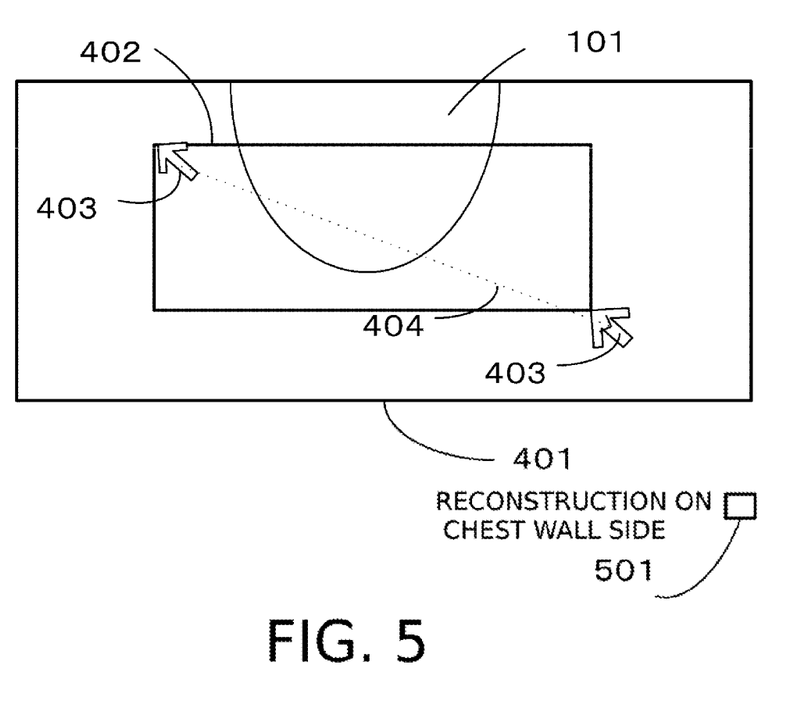
FIG. 5 is a conceptual diagram illustrating a method for inputting whether to perform image reconstruction of the chest wall side.

The system using the check box is not necessarily limiting, provided that the user can verify whether the reconstruction on the chest wall side can be performed. For example, a character string indicating the possibility of performing the reconstruction on the chest wall side may be displayed.

Figure 6:
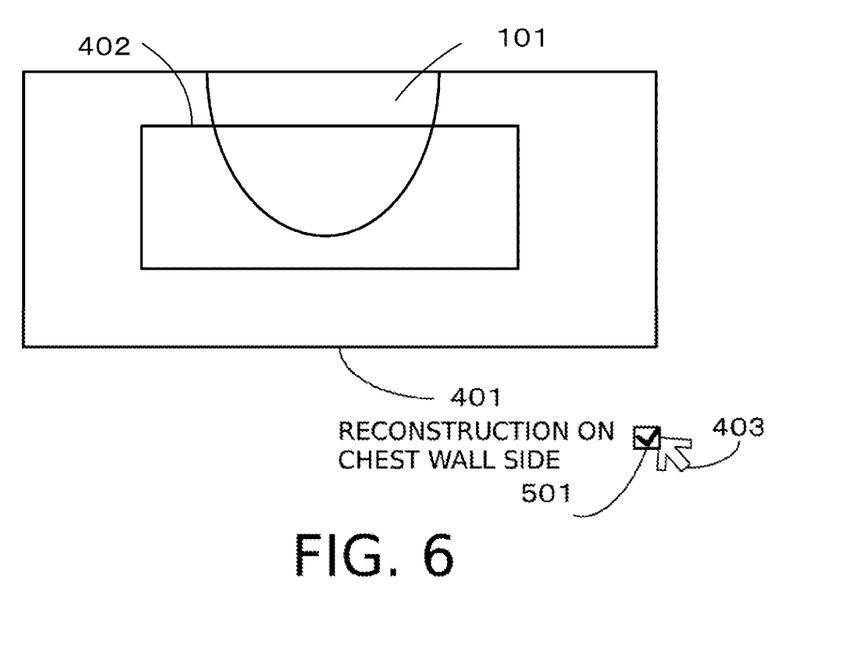
FIG. 6 is a conceptual diagram illustrating the state in which it is selected to perform image reconstruction of the chest wall side.

In step S304, the user selects whether to perform the reconstruction on the chest wall side. In the present embodiment, the check box 501 is checked (or displayed) in step S304. Accordingly, the user moves the cursor 403 by using a pointing device such as a mouse, as shown in FIG. 6, and checks the check box by clicking the mouse. A menu or the like for selecting whether to perform the reconstruction on the chest wall side may be also used in the region input unit 110, provided that the selection as to whether to perform the reconstruction on the chest wall side can be made.

Where the reconstruction on the chest wall side is to be implemented (S304=YES), the processing advances to step S305. Where the reconstruction is not to be implemented (S304=NO), the present flow is ended and the imaging is performed as usual with respect to the designated imaging region.

Figure 7:
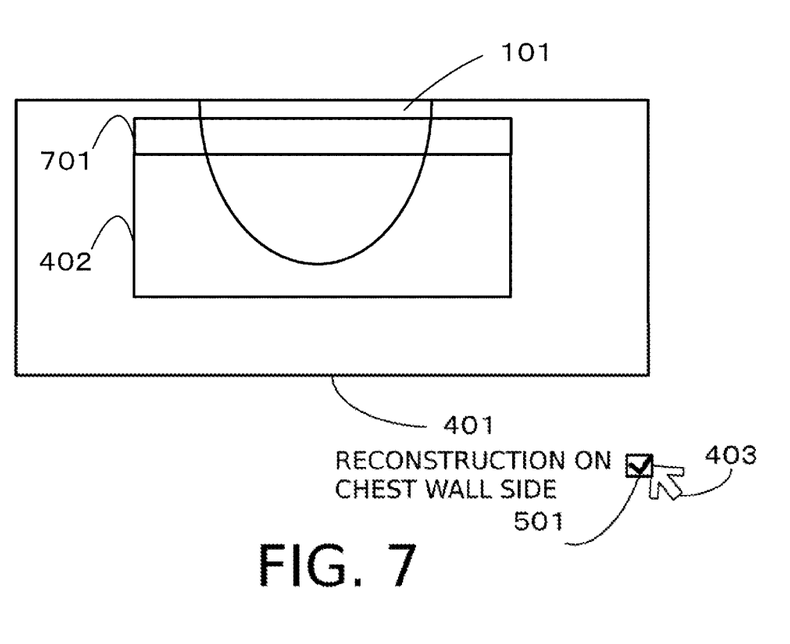
FIG. 7 is a conceptual diagram illustrating the state in which the reconstructed region on the chest wall side is added to the imaging region.

In step S305, as shown in FIG. 7, the display region (imaging region 402+reconstructed region 701 on the chest wall side) of the final reconstructed image obtained by adding the reconstructed region 701 on the chest wall side to the imaging region designated by the user in step S301 is displayed.

In step S306, information on the display region (imaging region 402+reconstructed region 701 on the chest wall side) obtained by adding the reconstructed region 701 on the chest wall side to the imaging region designated by the user and calculated in step S305 is transmitted to the scanning control unit 109 and the image construction unit 107.

In the scanning control unit 109, the position and range of scanning of the emission tip and the probe 104 are controlled by using the abovementioned information relating to the imaging region. In the image construction unit 107, image data processing is performed with respect to the abovementioned imaging region during image reconstruction.

In the present flow, where the check box 501 is checked in step S304, a region of a given size on the chest wall side is enlarged, but the user may also select (designate) the size of the reconstructed region on the chest wall side.

With the method of the present embodiment, the user can select whether to perform image reconstruction also with respect to the region in which the probe cannot be scanned due to the presence of the unit supporting the chest wall. As a result, the image of the object interior can be acquired within a wide range, even though of poor quality, and patient diagnostics can be improved.

Embodiment 2

Embodiment 2 of the present invention will be explained below. In the present embodiment, where the reconstruction of the region on the chest wall side is possible, it is performed uniformly, and whether to display this region is changed according to the user's selection. The configuration of the object information acquiring apparatus of the present embodiment is similar to that of Embodiment 1, but the function of the image construction unit 107 is different. Therefore, the explanation of the features same as those of Embodiment 1 is omitted and only the features different from those of Embodiment 1 are explained in detail.

Figure 8:
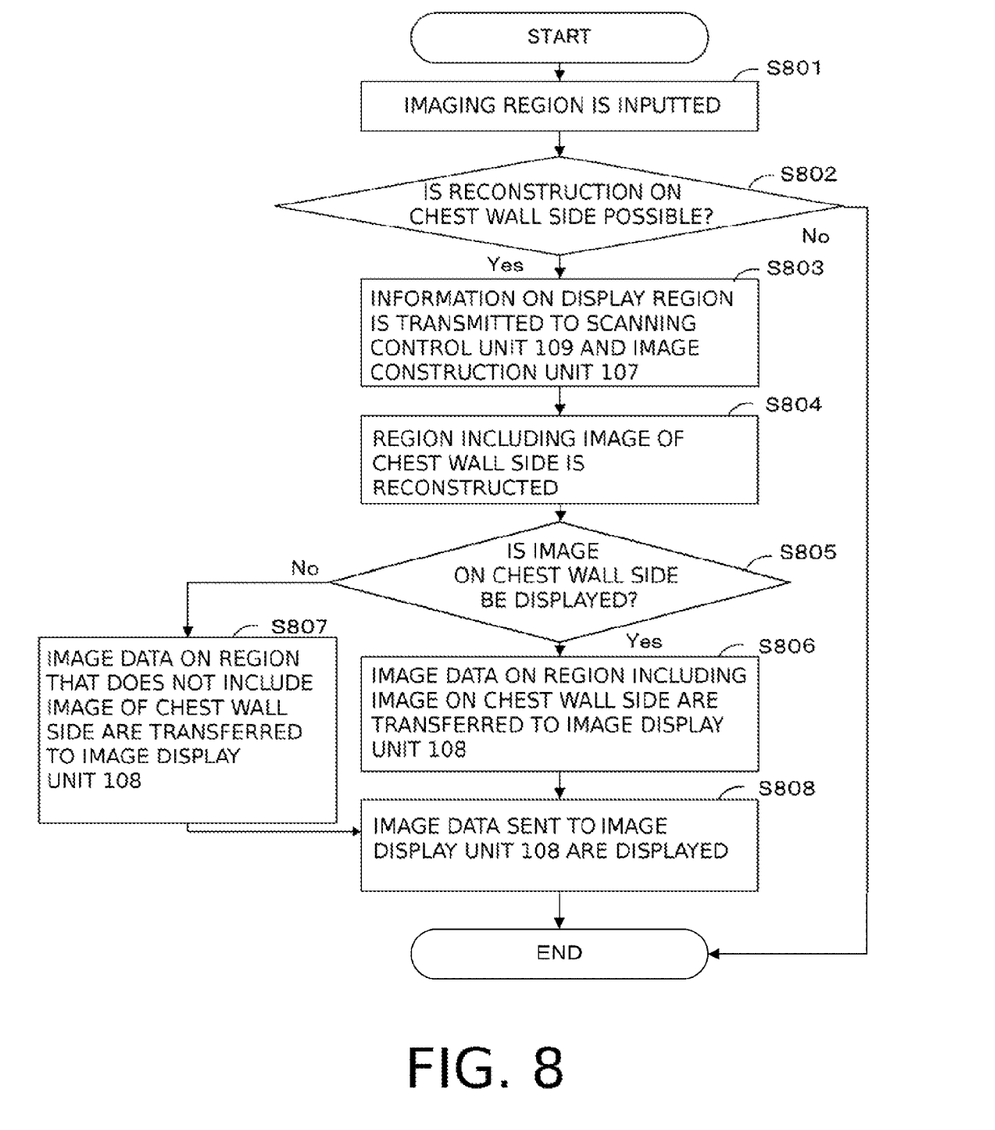
FIG. 8 is a flowchart illustrating the imaging sequence on the chest wall side in Example 2.

In the present embodiment, the user selects whether to display the image of the region (region with poor image quality) on the chest wall side in addition to the region with good image quality. The processing flow preceding actual display is explained below with reference to FIG. 8. FIG. 8 is a flowchart realized when the user designates the region for displaying the reconstructed image.

In step S801, the user designates the imaging region from the region input unit 110.

In step S802, it is determined whether or not the imaging region designated by the user is adjacent to the chest wall segment, that is, whether or not the probe during scanning can receive an acoustic wave from the chest wall. Where the acoustic wave on the chest wall side is received and the reconstruction is possible (S802=YES), the processing advances to S803. Meanwhile, where the region adjacent to the chest wall is not designated and the reconstruction on the chest wall side is impossible (S802=NO), the present flow is canceled and the usual photoacoustic imaging is performed.

In step S803, the information on the imaging region designated by the user in step S801 is transmitted to the scanning control unit 109 and the image construction unit 107.

In step S804, the scanning control unit 109 scans the emission tip and the probe 104 and picks up the image of the imaging region. In this case, the acoustic wave from the chest wall side adjacent to the imaging region can be also acquired. The image construction unit 107 then also performs image reconstruction with respect to the chest wall side in addition to the imaging region. In this case, information on the location of a boundary between the region with good image quality and the region with poor image quality can be also generated.

The region input unit 110 is provided with means enabling the user to select whether to display the chest wall side in step S805. Any means may be used as the selection means such as a check box or a selection menu. When the user selects the display of the chest wall image (S805=YES), the processing advances to step S806, and when non-display is selected (S805=NO), the processing advances to step S807.

In step S806, image data including the region on the chest wall side that have been held in the reconstruction unit 107 are transferred to the image display unit 108. In this case, the information relating to the boundary of regions with different image quality may be transferred at the same time.

Meanwhile, in step S807, image data which do not include the region on the chest wall side, from among the image data held in the reconstruction unit 107, are transferred to the image display unit 108.

In step S808, image data transferred in step S806 or S807 are displayed by the image display unit 108. When the region including the region on the chest wall side is displayed, the user can discriminate the region that is not on the chest wall side by coloration or the like.

With the method of the present embodiment, the user can select whether to display the reconstructed image with respect to the region where the probe cannot be scanned. As a result, the image of the object interior can be acquired within a wide range, even though of a poor quality, and patient diagnostics can be improved.

Embodiment 3

In the above-described embodiment, a portion of a breast inserted between a pair of plate-shaped members, this portion being close to the chest wall, is explained by way so example as a region with poor image quality. Thus, in this region, the probe movement to the front surface is impeded by the unit for supporting the chest wall of the patient in a prone position. In those embodiments, an image of poor quality can be obtained for such a region by using the ultrasound wave which is incident obliquely on the probe. In addition the user can select whether to obtain the image despite its poor quality and whether to display the obtained image.

However, the imaging using the ultrasound wave which is incident obliquely on the probe is not limited only to the vicinity of the chest wall. In photoacoustic measurements, the light emitted from the irradiating unit facing the probe typically propagates and diffuses also into an object region other than that directly on the probe (on the normal to the holding plate), and photoacoustic waves are thus generated. Further, the probe can also receive such an acoustic wave incident from the oblique direction, although the sensitivity of reception with respect to this wave is lower than that with respect to the acoustic wave incident in the direction perpendicular to the receiving surface. Therefore, the acoustic wave incident obliquely on the probe can be also used with respect to the region other than the vicinity of the chest wall.

For example, when a breast is held between the holding units, a technique of thinly compressing the breast is used to allow the light to reach the deeper zones of the object and increase the intensity of acoustic wave. However, such compression places a burden on the patient and therefore, a shorter period of time in which the breast is compressed is preferred. In other words, it is desirable to narrow the scanning range in order to shorten as much as possible the measurement time in which the breast is compressed. From this standpoint, where the user (health-care professional) designates only the minimum necessary region for measurements, it may be desirable to obtain the image with respect to the periphery of the designated region, even though this image is of poor quality.

As a separate example, the case can be also considered in which a standing patient places a breast on a holding unit for photoacoustic measurements. In such a case, where the patient stands upright for a long time, the burden thereon also increases. Therefore, a shorter measurement time is preferred.

According to the present embodiment, the user can select whether to display the reconstructed image, even though of degraded image quality, not only with respect to the chest wall vicinity, but also with respect to the periphery of the region where the probe is scanned. As a result, the volume of information on the object provided to the user can be larger than that in the conventional apparatuses when the measurement time is shortened to reduce the burden on the patient.

Further, the probe is not necessarily scanned by a scanning mechanism. The present invention can be also used with the configuration that enables the user to select whether to display the image based on the acoustic wave from a portion other than the region measured by the probe located opposite thereto.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-86310, filed on Apr. 5, 2012, which is hereby incorporated by reference herein in its entirety.

What is claimed is:

1. An object information acquiring apparatus comprising:
   an irradiating unit configured to irradiate an object with light;
   a probe configured to receive an acoustic wave generated from the object irradiated with the light;
   a scanning unit configured to move said probe relative to the object to scan the object;
   an imaging region input unit configured to receive an input of a designation of an imaging region, which is a region of the object to be scanned by said probe and from which the acoustic wave is received by said probe;
   a generating unit configured to generate an image of an object interior on the basis of the acoustic wave received by the probe; and
   a display region input unit configured to receive an input of a designation of a display region, which is a region of the object whose image is generated by said generating unit and displayed,
   wherein said display region input unit is further configured to receive a selection as to whether to display an image of an adjacent region, on the basis of the acoustic wave received by the probe while scanning said imaging region, the adjacent region being a region adjacent to the imaging region and which has not been faced by said probe.

2. The object information acquiring apparatus according to claim 1, wherein
   the object is a patient's breast held by a holding unit,
   said probe is configured to scan the holding unit and receive an acoustic wave from an imaging region of the breast designated by a user with said imaging region input unit, and
   said display region input unit is configured to receive a selection as to whether to display a generated image with respect to a region which is a region of the breast that is adjacent to the imaging region and in which the probe scanning cannot be performed due to a chest wall of the patient.

3. The object information acquiring apparatus according to claim 1, further comprising a display unit configured to display the generated image of the designated display region.

4. The object information acquiring apparatus according to claim 3, wherein when the selection to display the generated image of the adjacent image is inputted, said display unit displays the generated image by using the imaging region and the adjacent region as the display regions.

5. The object information acquiring apparatus according to claim 4, wherein said generating unit is configured to determine a region for generating an image on the basis of a display region for which the display region input unit has received a designation input.

6. The object information acquiring apparatus according to claim 4, wherein said generating unit is configured to generate images of the imaging region and the adjacent region, and transmit the generated images to said display unit on the basis of a display region for which said display region input unit has received a designation input.

7. The object information acquiring apparatus according to of claim 4, wherein said display unit is configured to perform display such that the imaging region and the adjacent region can be discriminated from each other in the display region.

8. An information processing apparatus comprising:
  a generating unit configured to generate an image of an object interior on the basis of an acoustic wave induced by an irradiation of the object with light and received by a probe moving relative to the object while changing a portion of the object facing the probe;
  an imaging region input unit configured to receive an input of a designation of an imaging region, which is a region of the object to be scanned by said probe and from which the acoustic wave is received by said probe;
  a display region input unit configured to receive an input of a designation of a display region, which is a region of the object whose image is displayed,
  wherein said display region input unit is further configured to receive a selection as to whether to display an image of an adjacent region, on the basis of the acoustic wave received by the probe while scanning said imaging region, the adjacent region being a region adjacent to the imaging region and which has not been faced by said probe.

9. The information processing apparatus according to claim 8, further comprising a display unit configured to display the generated image of the designated display region.

10. The information processing apparatus according to claim 9, wherein said display unit is configured to, when the selection to display the generated image of the adjacent image is inputted, display the generated image by using the imaging region and the adjacent region as the display regions.

11. The information processing apparatus according to claim 10, wherein said generating unit is configured to determine a region for generating an image on the basis of a display region for which the display region input unit has received a designation input.

12. The information processing apparatus according to claim 10, wherein said generating unit is configured to generate images of the imaging region and the adjacent region, and transmit the generated images to said display unit on the basis of a display region for which said display region input unit has received a designation input.

13. The information processing apparatus according to of claim 10, wherein said display unit is configured to perform display of the imaging region and the adjacent region in different manners such that the imaging region and the adjacent region can be discriminated from each other in the display region.

14. A control method of an object information acquiring apparatus comprising:
  generating, using a generating unit, an image of an object interior on the basis of an acoustic wave induced by an irradiation of light to the object and received by a probe moving relative to the object changing a portion of the object facing the probe;
  receiving, using an imaging region input unit, an input of a designation of an imaging region, which is a region of the object to be scanned by said probe and from which the acoustic wave is received by said probe;
  receiving, via a display region input unit, an input of a designation of a display region, which is a region of the object whose image is displayed;
  further receiving, via the display region input unit, a selection as to whether to display an image of an adjacent region, on the basis of the acoustic wave received by the probe while scanning said imaging region, the adjacent region being a region adjacent to the imaging region and which has not been faced by the probe.

15. The control method of the object information acquiring apparatus according to claim 14, further comprising:
  displaying, on a display unit, the generated image of the designated display region.

16. The control method of the object information acquiring apparatus according to claim 15, wherein, in said step of receiving the selection to display the generated image of the adjacent image is inputted, the display unit displays the generated image by using the imaging region and the adjacent region as the display regions.

17. The control method of the object information acquiring apparatus according to claim 16, wherein, in said generating step, the generating unit determines a region for generating an image on the basis of a display region for which the display region input unit has received a designation input.

18. The control method of the object information acquiring apparatus according to claim 16, wherein, in said generating step, the generating unit generates images of the imaging region and the adjacent region, and transmit the generated images to the display unit on the basis of a display region for which the display region input unit has received a designation input.

19. The control method of the object information acquiring apparatus according to claim 16, wherein, in said displaying step, the display unit performs display such that the imaging region and the adjacent region can be discriminated from each other in the display region.

* * * * *